United States Patent [19]

Wasley

[11] Patent Number: 4,596,799
[45] Date of Patent: Jun. 24, 1986

[54] 9H-PYRROLO[2,1-C]-1,2,4-TRIAZOLO[4,3-A][1,4]BENZODIAZEPINES

[75] Inventor: Jan W. F. Wasley, Chatham, N.J.

[73] Assignee: Ciba-Geigy Corporation, Ardsley, N.Y.

[21] Appl. No.: 696,295

[22] Filed: Jan. 29, 1985

[51] Int. Cl.$^4$ .................. C07D 487/14; A61K 31/55
[52] U.S. Cl. .................. 514/219; 260/245.5; 260/244.4; 260/243.3
[58] Field of Search ............... 260/245.5, 243.3, 244.4; 514/219

[56] References Cited

U.S. PATENT DOCUMENTS

| | | | |
|---|---|---|---|
| 3,876,634 | 4/1975 | Meguro et al. | 260/245.5 |
| 3,947,417 | 3/1976 | Kuwata et al. | 260/245.5 |
| 4,192,803 | 0/1980 | Wright et al. | 260/243.3 |
| 4,362,666 | 12/1982 | Wasuy | 260/245.7 |
| 4,404,137 | 9/1983 | Chakrabarti et al. | 260/239.3 T |
| 4,424,221 | 0/1984 | Wasley | 424/250 |
| 4,464,300 | 8/1984 | Borer et al. | 260/245.5 |
| 4,479,955 | 0/1984 | Yokoyama | 424/251 |
| 4,492,699 | 1/1985 | Chakrabarti et al. | 260/243.3 |
| 4,508,716 | 4/1985 | Liepmann et al. | 260/243.3 |
| 4,521,534 | 0/1985 | Gauthier et al. | 514/219 |
| 4,542,131 | 9/1985 | Chakrabarti et al. | 260/243.3 |

FOREIGN PATENT DOCUMENTS 2244450  3/1973  Fed. Rep. of Germany ... 260/245.5

OTHER PUBLICATIONS

J. Med. Chem. 23, 462 (1980)—Wright et al.
Annual Reports in Med. Chem., 20, (1985)—pp. 1-9, Petrack et al.
Drugs, 19, pp. 195-219—Benzodiazepines—Bellantuono et al. (1980).
Proc. Natl. Acad. Sci. U.S.A., 74, No. 9, pp. 3805-3809, Braestrup et al., (1977).
Nature, 275, pp. 551-553—Williamson et al. (1978).
European J. of Pharmacology, 48, pp. 213-218, Chang et al, (1978).
Nature, 266, pp. 732-734, Squires, (1977).
J. Het. Chem., 22, pp. 305-310, Duceppe et al, (1985).

*Primary Examiner*—Glennon H. Hollrah
*Assistant Examiner*—Dara Dinner
*Attorney, Agent, or Firm*—Norbert Gruenfeld

[57] ABSTRACT

Disclosed are the novel compounds of formula I

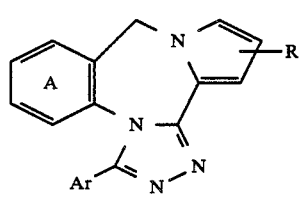

wherein ring A is unsubstituted or substituted by one or two identical or different substituents selected from lower alkyl, halogen, trifluoromethyl, lower alkoxy, hydroxy and acyloxy; or ring A is substituted on adjacent carbon atoms by lower alkylenedioxy; R represents hydrogen, halogen or lower alkyl; and Ar represents carbocyclic aryl or heteroaryl;

which are useful as benzodiazepine receptor agonists, processes for preparing the same, pharmaceutical compositions comprising said compounds and methods of treating nervous system disorders, such as anxiety and epilepsy, by administration of said compounds and pharmaceutical compositions to mammals.

18 Claims, No Drawings

9H-PYRROLO[2,1-C]-1,2,4-TRIAZOLO[4,3-A][1,4]BENZODIAZEPINES

SUMMARY OF THE INVENTION

The present invention is directed to 3-aryl-9H-pyrrolo[2,1-c]-1,2,4-triazolo[4,3-a][1,4]-benzodiazepines which are benzodiazepine receptor ligands and modulators, particularly agonists, demonstrating useful nervous system regulatory activity, e.g. psychoactive, such as anxiolytic, and anticonvulsant activity.

The foregoing attributes render the compounds of this invention particularly useful when administered, alone or in combination, to mammals for the treatment of nervous system disorders, such as anxiety and convulsive conditions (epilepsy).

DETAILED DISCLOSURE OF THE INVENTION

This invention relates to the novel 3-aryl-9H-pyrrolo[2,1-c]-1,2,4-triazolo[4,3-a][1,4]-benzodiazepines of formula I useful e.g. as benzodiazepine receptor agonists, processes for preparing the same, pharmaceutical compositions comprising said compounds and methods of treating nervous system disorders, such as anxiety and epilepsy, by administration of said compounds and pharmaceutical compositions to mammals.

Particularly the invention relates to compounds of the formula I

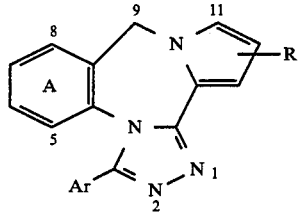

wherein ring A is unsubstituted or substituted by one or two identical or different substituents selected from lower alkyl, halogen, trifluoromethyl, lower alkoxy, hydroxy and acyloxy; or ring A is substituted on adjacent carbon atoms by lower alkylenedioxy; R represents hydrogen, halogen or lower alkyl; Ar represents carbocyclic aryl or heteroaryl, preferably (a) phenyl or phenyl substituted by one or two identical or different substituents selected from lower alkyl, halogen, trifluoromethyl, lower alkoxy, hydroxy and acyloxy; or phenyl substituted on adjacent carbon atoms by lower alkylenedioxy;

(b) naphthyl or naphthyl substituted by one or two identical or different substituents selected lower alkyl, halogen, lower alkoxy, hydroxy and acyloxy;

(c) pyridinyl or pyridinyl substituted on carbon by one or two substituents selected from lower alkyl, lower alkoxy and halogen;

(d) pyrrolyl or pyrrolyl substituted on carbon by one or two substituents selected from lower alkyl, lower alkoxy and halogen; or said radical substituted on nitrogen by lower alkyl;

(e) quinolinyl or isoquinolinyl or each said radical substituted on carbon by one or two substituents selected from lower alkyl, lower alkoxy, halogen and hydroxy;

(f) imidazolyl or imidazolyl substituted on carbon by one substituent selected from lower alkyl and halogen; or said radical substituted on one nitrogen by lower alkyl;

(g) thienyl or thienyl substituted on carbon by one or two substituents selected from lower alkyl, lower alkoxy or halogen;

(h) furanyl or furanyl substituted on carbon by one or two lower alkyl groups;

(i) pyrimidinyl or pyrimidinyl substituted or carbon by one or two substituents selected from lower alkyl, lower alkoxy and halogen;

(j) pyrazinyl or pyrazinyl substituted on carbon by one or two lower alkyl groups;

(k) thiazolyl or thiazolyl substituted on carbon by one substituent selected from lower alkyl and halogen; and (l) indolyl or indolyl substituted on carbon by one or two substituents selected form lower alkyl, lower alkoxy and halogen; or said radical substituted on nitrogen by lower alkyl;

wherein the point of attachment of any of the said heteroaryl radicals is on a ring carbon; and wherein the point of attachment for pyrrolyl, indolyl or imidazolyl radicals unsubstituted on nitrogen may also be on ring nitrogen; and pharmaceutically acceptable salts thereof.

A preferred embodiment of the invention relates to the compounds of the formula II

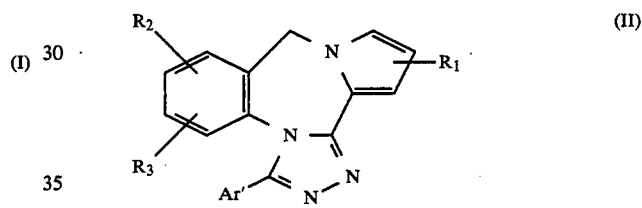

wherein Ar' represents 2-, 3- or 4-pyridinyl or 2-, 3- or 4-pyridinyl monosubstituted on carbon by lower alkyl, lower alkoxy or halogen; $R_1$ represents hydrogen, lower alkyl or halogen; $R_2$ and $R_3$ independently represent hydrogen, lower alkyl, halogen, trifluoromethyl, lower alkoxy, hydroxy, or acyloxy in form of a pharmaceutically acceptable ester; or $R_2$ and $R_3$ together on adjacent carbon atoms represent lower alkylenedioxy; and pharmaceutically acceptable salts thereof.

Preferred are the compounds of formula II wherein Ar' represents 2-pyridinyl or 2-pyridinyl monosubstituted on carbon by lower alkyl, lower alkoxy or halogen.

Further preferred are the compounds of formula II wherein Ar' represents 2-pyridinyl; $R_1$ represents hydrogen, lower alkyl or halogen; $R_2$ represents hydrogen, lower alkoxy, lower alkyl, halogen or trifluoromethyl; $R_3$ represents hydrogen, halogen, lower alkyl or lower alkoxy; or $R_2$ and $R_3$ together on adjacent carbon atoms represent methylenedioxy; and pharmaceutically acceptable salts thereof.

Highly preferred are said compounds of formula II wherein Ar' represents 2-pyridinyl; $R_1$ represents hydrogen; $R_2$ represents hydrogen, halogen or trifluoromethyl; $R_3$ represents hydrogen; and pharmaceutically acceptable salts thereof.

Other preferred embodiments of the invention relate to the compounds of formula I wherein ring A is unsubstituted or mono- or disubstituted independently of each other by halogen, lower alkyl or lower alkoxy; or monosubstituted by trifluoromethyl; R represents hydrogen; Ar represents phenyl or phenyl monosubstituted by halogen, trifluoromethyl or lower alkyl; or Ar represents 2- or 3-thienyl; and pharmaceutically acceptable salts thereof.

The general definitions used herein have the following meaning within the scope of the present invention.

Halogen is preferably chloro, but may also be fluoro, bromo or iodo.

The term "lower" referred to above and hereinafter in connection with organic radicals or compounds respectively defines such with up to and including 7, preferably up to and including 4 and advantageously one or two carbon atoms.

Lower alkyl contains 1 to 7 carbon atoms, preferably 1 to 4 carbon atoms, is advantageously straight chain and represents for example methyl, ethyl, propyl or butyl, advantageously methyl.

Lower alkoxy is preferably straight chain alkoxy containing 1 to 4 carbon atoms and represents for example methoxy, ethoxy, propoxy, advantageously methoxy.

Lower alkylenedioxy is preferably ethylenedioxy or methylenedioxy.

Aryl represents optionally substituted carbocyclic aryl or heterocyclic aryl.

Carbocyclic aryl represents phenyl or naphthyl optionally substituted preferably by halogen, lower akyl, lower alkoxy, hydroxy, acyloxy or lower alkylenedioxy.

Heteroaryl represents mono- or bicyclic heteroaryl, preferably pyridinyl, pyrrolyl, quinolinyl, isoquinolyl, imidazolyl, thienyl, furanyl, pyrimidinyl, thiazolyl, pyrazinyl or indolyl, each optionally substituted preferably by lower alkyl, lower alkoxy, halogen, hydroxy or acyloxy.

Acyloxy is preferably in the form of a pharmaceutically acceptable ester and represents preferably lower alkanoyloxy, aroyloxy, di-lower alkylcarbamoyloxy or lower alkoxycarbonyloxy.

Lower alkanoyloxy is preferably acetoxy, pivaloyloxy (trimethylacetoxy), propionyloxy.

Aroyloxy is preferably benzoyloxy or benzoyloxy substituted on the benzene ring by one to three of lower alkyl, lower alkoxy, halogen or trifluoromethyl, or heteroaroyloxy.

Heteroaroyloxy is preferably 2-thienoyloxy, or 2-, 3- or 4-pyridinylcarbonyloxy, advantageously nicotinoyloxy.

Lower alkoxycarbonyloxy is preferably methoxycarbonyloxy, ethoxycarbonyloxy, propoxycarbonyloxy or butoxycarbonyloxy.

Di-lower alkylcarbamoyloxy is preferably di-N-(methyl, ethyl, propyl)-carbamoyloxy.

Naphthyl represents 1- or 2-naphthyl, advantageously 2-naphthyl.

Pyridinyl represents 2-, 3- or 4-pyridinyl, advantageously 2-pyridinyl.

Pyrrolyl represents 2- or 3-pyrrolyl, preferably 2-pyrrolyl.

Quinolinyl represents preferably 2-, 3- or 4-quinolinyl, advantageously 2-quinolinyl.

Isoquinolinyl represents preferably 1-, 3- or 4-isoquinolinyl, advantageously 3-isoquinolyl.

Imidazolyl represents preferably 4- or 5-imidazolyl.

Thienyl represents 2- or 3-thienyl.

Furanyl represents 2- or 3-furanyl, preferably 2-furanyl.

Pyrimidinyl represents 2-, 4- or 5-pyrimidinyl, preferably 2- or 4-pyrimidinyl.

Thiazolyl represents 2,- 4-, or 5-thiazolyl, preferably 4-thiazolyl.

Indolyl represents preferably 2- or 3-indolyl, advantageously 2-indolyl.

Pyrazinyl represents 2-pyrazinyl.

Pharmaceutically acceptable salts are acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic sulfonic acids, e.g. methanesulfonic acid, ethanesulfonic acid, hydroxyethanesulfonic, benzenesulfonic, p-toluenesulfonic or naphthalenesulfonic.

For the compounds of formula I wherein Ar represents a basic heteroaryl radical, e.g. optionally substituted pyridinyl, quinolinyl, imidazolyl, pyrimidinyl, pharamceutically acceptable salts are also acid addition salts of aliphatic or aromatic carboxylic acids e.g. acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicyclic, 4-aminosalicyclic, pamoic, nicotinic acid; or ascorbic acid.

For said compounds of formula I wherein Ar represents a basic heteroaryl radical pharmaceutically acceptable salts also include the bis acid addition salts resulting from protonation at two sites with a strong acid such as listed above.

The novel compounds of the invention are active in state of art in vitro and in vivo test systems which have been correlated with effectiveness for the treatment of nervous system disorders in mammals, including man, e.g. of anxiety and convulsive disorders.

The compounds of the invention exhibit valuable pharmacological properties, e.g. nervous system regulatory effects, by inter alia modulating the benzodiazepine receptor activity in mammals. The compounds are thus useful for the treatment of nervous system diseases, e.g. those responsive to benzodiazepine receptor stimulation.

The compounds of the invention bind to the benzodiazepine receptor and exhibit e.g. anxiolytic and/or anticonvulsant effects. Said effects are demonstrable by in vitro and in vivo tests, using advantageously mammals, e.g. mice, rats, or monkeys, as test objects. Said compounds can be applied to them enterally or parenterally, advantageously orally, subcutaneously, intravenously or intraperitoneally, for example, within gelatin capsules or in the form of aqueous solutions or suspensions respectively. The applied dosage may range between about 0.01 and 100 mg/kg/day, preferably between about 0.5 and 50 mg/kg/day, advantageously between about 1 and 30 mg/kg/day. The applied dosage in vitro may range between about $10^{-6}$ and $10^{-10}$M concentration, preferably between about $10^{-7}$ and $10^{-9}$M.

The benzodiazepine receptor binding properties indicative of the nervous system regulatory activity of said new compounds are determined in the receptor binding assay in vitro, e.g. similarly to that in Nature 266, 732 (1977) or Proc. Nat. Acad. Sci. USA 74, 3805 (1977), using tritiated flunitrazepam as the radioactive ligand. The concentration of the compounds of this invention, required to inhibit the specific binding of 0.5 nM of tritiated flunitrazepam by 50%, i.e. the IC$_{50}$, is determined graphically.

In vivo benzodiazepine receptor binding is determined essentially as described in Eur. J. Pharmacol. 48, 213 (1978) and Nature 275, 551 (1978). Test compounds in a corn starch vehicle are administered orally or intraperitoneally to mice or rats. A decrease in the binding of $^3$H-flunitrazepam in the brain of drug-treated animals (as compared with the binding observed in animals treated with vehicle alone) is indicative of benzodiazepine receptor binding by the test compound.

Anxiolytic effects are observed, for example, according to the Cook-Davidson conflict procedure, using male Wistar rats, as described e.g. in U.S. Pat. No. 4,479,955. A drug-induced enhancement of performance is indicative of antianxiety effects.

Anticonvulsant effects are observed, for example in the standard Metrazole (pentylenetetrazole) test for assessing anticonvulsant activity, e.g. orally in the rat as described in U.S. Pat. No. 4,479,955.

Illustrative of the invention, the compounds of examples 1, 3, 7f and 4 exhibit an $IC_{50}$ of about 4.0, 0.7, 1.0 and 0.4 nM respectively, in the in vitro benzodiazepine receptor assay.

Also illustrative of the invention, the compounds of Examples 1, 3, 7f and 4 inhibit flunitrazepam binding in vivo by about 67% at 30 mg/kg p.o., 50% at 5.3 mg/kg p.o., 75% at 30 mg/kg p.o., 50% at 0.6 mg/kg p.o., respectively, in the mouse.

Illustrative of the anxiolytic effect of the compounds of the invention, the compound of Example 1 is effective in the Cook-Davidson assay in the rat at a dose of about 0.3 mg/kg p.o.

Illustrative of the anticonvulsant activity of the compounds of the invention, the compound of Example 1 is effective in the metrazole assay in the rat, with an $ED_{50}$ of about 3 mg/kg p.o.

Accordingly, the compounds of the invention are useful as nervous system active agents, e.g. as benzodiazepine receptor agonists, for example for the treatment or management of nervous system disorders, such as anxiety, convulsive conditions (epilepsy) or other disorders in mammals responsive to said benzodiazepine receptor modulation. They are also useful in the preparation of other valuable products, especially of pharmacologiically active pharmaceutical compositions.

The compounds of the invention, i.e. the compounds of formula I or II and salts, are advantageously prepared by methods using chemical reactions known per se, according to the following processes:

(a) cyclizing a compound of formula III

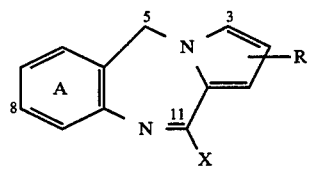

(III)

wherein ring A and R have meaning as defined hereinabove, and X represents ArCONHNH— in which Ar has meaning as defined above;

(b) condensing a compound of the formula IIIa,

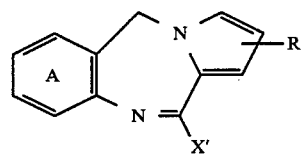

(IIIa)

wherein ring A and R have meaning as defined above, and wherein X' represents a leaving group, preferably lower alkoxy, lower alkylmercapto, reactive esterified hydroxy e.g. halogen, or cyanothio; with a compound of the formula IV

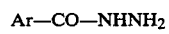

Ar—CO—NHNH$_2$ (IV)

wherein Ar has meaning as defined above;

(c) condensing a compound of formula IIIb

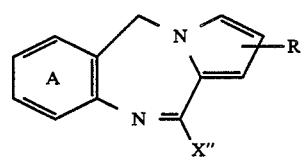

(IIIb)

wherein ring A and R have meaning as defined hereinabove, and wherein X" represents hydrazino; with a compound of the formula V

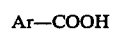

Ar—COOH (V)

wherein Ar has meaning as defined hereinabove, or a reactive functional derivative thereof;

(d) condensing a compound of the formula VI

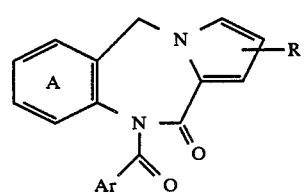

(VI)

wherein ring A, R and Ar have meaning as defined hereinabove, with hydrazine;

and in all the above processes, if necessary, temporarily protecting any interfering reactive groups(s) and then isolating the resulting compound of the formula I; and, if desired, converting a resulting compound of formula I into another compound of the invention, and/or, if desired, converting a resulting free compound into a salt or a resulting salt into a free compound or into another salt, and/or, if required, separating a mixture of isomers obtained into the single isomers.

In starting compounds and intermediates which are converted to the compounds of the invention in a manner described herein, functional groups present, such as carboxy, amino and hydroxy, are optionally protected by conventional protecting groups that are common in preparative organic chemistry. Protected carboxy, amino and hydroxy groups are those that can be converted under mild conditions into free carboxy, amino and hydroxy groups without the molecular framework being destroyed or other undesired side reactions taking place.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, N.Y. 1984, and also in Houben-Weyl, "Methoden der Organischen Chemie", Vol. 15/1, George Thieme Verlag, Stuttgart, 1974.

A reactive functional derivative of a carboxylic acid of formula V above represents e.g. an acyl halide such as the acid chloride, the anhydride of said acid, a mixed anhydride e.g. such derived from a lower alkyl halocarbonate such as ethyl chloroformate, a reactive ester, e.g. a lower alkyl ester such as an ethyl or methyl ester or an optionally substituted phenyl ester, or an amide, e.g. such derived for imidazole (prepared from N,N-carbonyldiimidazole).

Reactive esterified hydroxy as represented by, e.g. X' in compounds of formula IIIa, is hydroxy esterified by a strong acid, especially a strong inorganic acid, such as a hydrohalic acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methylsulfonyloxy or 4-methylphenylsulfonyloxy (tosyloxy).

The cyclization according to process (a) is carried out preferably in an inert anhydrous solvent, such as ethanol, dimethylformamide, diglyme or ethylene dichloride, advantageously at a temperature ranging from about 50° to 150° C., preferably about 60° to 110° C., with or without a dehydrating or drying agent such as molecular sieves, or under azeotropic conditions, such as are well-known in the art, for removal of the liberated water.

The starting materials for process (a) of formula III wherein X=ArCONHNH—, are in turn prepared by condensation of a compound of formula IIIa as defined under process (b) with a compound of formula IV as defined above, e.g. in an inert solvent such as methylene chloride or ethylene dichloride, preferably at room temperature or at a temperature up to about 50° C. with or without a basic catalyst such as triethylamine or potassium carbonate.

The intermediates of formula III, IIIa, IIIb and VI are prepared by known general chemical methodology from the corresponding compounds of formula IIIc

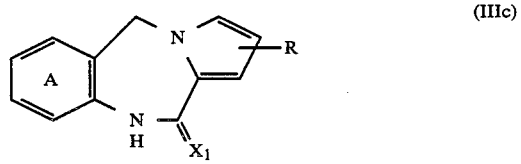

(IIIc)

wherein ring A and R have meaning as defined above and $X_1$ represents oxygen or sulfur. The compounds of formula IIIc may also be represented in the tautomeric form corresponding to formula IIIa above but wherein X' represents hydroxy or mercapto.

The intermediates of formula IIIc are either known or, if new, are prepared according to methodology described in U.S. Pat. No. 4,192,803 and J. Med. Chem. 23, 462 (1980), or modifications as described in the examples.

Furthermore, the compounds of formula IIIc wherein R represents hydrogen may be converted to compounds of formula IIIc wherein R represents halogen, by halogenation with e.g. chlorine or bromine in acetic acid, N-bromosuccinimide or N-chlorosuccinimide in an inert solvent such as tetrahydrofuran, aluminum bromide or aluminum chloride in an inert solvent such as methylene chloride.

The condensation according to process (b) is carried out preferably in an inert solvent, such as ethanol, dimethylformamide, diglyme, ethylene dichloride, advantageously at a temperature ranging from about 50° to 150° C., preferably about 50° to 100° C., optionally in the presence of a dehydrating or drying agent such as molecular sieves, and optionally in the presence of a basic catalyst such as triethylamine or potassium carbonate, if required.

The starting materials of formula IIIa are prepared from the compounds of formula IIIc using methodology well-known in the art. For example, a compound of formula IIIa wherein X' represents chloro is prepared by treatment of the correspondingly substituted compound of formula IIIc wherein $X_1$ represents oxygen with phosphorous oxychloride in a appropriate solvent, e.g. methylene chloride.

The starting materials of formula IV are either known or are prepared by methods well-known in the art, e.g. by condensation of a reactive functional derivative of the carboxylic acid of formula V with hydrazine.

The condensation according to process (c) is carried out preferably in an inert solvent such as dimethylformamide or ethylene dichloride, advantageously at a temperature ranging from about 50° to 100° C., optionally in the presence of catalyst appropriate to the nature of the starting material used, e.g. a reactive functional derivative of the carboxylic acid of formula V or the free carboxylic acid of formula V, under conditions analogous to those known in the art for the formation of an amide bond.

The starting materials of formula IIIb are prepared e.g. by condensation of a compound of formula IIIa with hydrazine in an inert solvent preferably at elevated temperature.

The starting materials of formula VI are prepared by conensation of a compound of formula IIIc with a reactive functional derivative of a compound of formula V in the presence of a strong anhydrous base, e.g. sodium hydride in dimethylformamide.

The compounds of the invention obtained by the above-cited processes can be converted into other compounds of the invention of formula I according to methodology known in the art.

Compounds of formula I wherein R represents hydrogen may be converted to the corresponding compounds of formula I with R being halogen, especially chloro or bromo, by halogenation with e.g. chlorine in acetic acid, N-bromosuccinimide or N-chlorosuccinimide solvent such tetrahydrofuran, or aluminum bromide or aluminum chloride in an inert solvent such as methylene chloride.

Compounds of formula I wherein R represents halogen, especially chloro or bromo at position 11, may be converted to the corresponding compounds of formula I wherein R represents hydrogen, by hydrogenolysis, e.g. with hydrogen in the presence of a hydrogenation catalyst such as palladium on charcoal.

Compounds of formula I, substituted by e.g. an acyloxy group, such as lower alkanoyloxy or aroyloxy, may be converted to compounds of formula I substituted by hydroxy, by hydrolysis with e.g. aqueous acid such as hydrochloric acid, or with aqueous alkali, such as lithium or sodium hydroxide.

Conversely, the conversion of compounds of formula I substituted by hydroxy to compounds of formula I substituted by acyloxy, such as alkanoyloxy or aroyloxy, may be carried out by condensation with a corresponding carboxylic acid, or a reactive functional derivative thereof, according to acylation (esterification) procedures well-known to the art.

The conversion of the compounds of formula I substituted by an etherified hydroxy group, e.g. lower alkoxy, to the compounds of formula I substituted by a hydroxy group is carried out by methods well-known in the art, e.g., with a mineral acid, such as hydriodic acid or, advantageously for compounds wherein lower alkoxy is methoxy, with e.g. boron tribromide in methylene chloride or with sodium or lithium diphenylphosphide in tetrahydrofuran.

With reference to the above reactions and as mentioned above, it may be advantageous to appropriately protect the potentially reactive, e.g., hydroxy, or other interfering substituents in accordance with protective techniques well-known to the art, e.g. as illustrated below, such that interfering reactions are avoided, by protecting such substituents prior to the desired reaction and subsequently, if necessary removing the protective groups to obtain the desired compounds, of formula I, or intermediates.

A hydroxy group may be protected in the form of esters, e.g. as acyl derivatives such as the lower alkanoyl, benzyloxycarbonyl or lower alkoxycarbonyl esters, or such hydroxy group may be protected in the form of ethers, e.g. as the 2-tetrahydropyranyl, or benzyl ethers.

In a resulting protected compound of formula I or intermediate, in which one or more of the functional groups are protected, the protected functional groups, e.g. hydroxy groups can be liberated, in a manner, known per se, e.g. by means of solvolysis, especially hydrolysis with acid, or by means of reduction, especially hydrogenolysis.

The above-mentioned reactions are carried out according to standard methods, in the presence or absence of diluents, preferably such as are inert to the reagents and are solvents thereof, of catalysts, condensing or said other agents respectively and/or inert atmosphere, at low temperatures, room temperature or elevated temperatures preferably near the boiling point for the solvents used, at atmospheric or superatomospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts. Whenever desirable, the above processes are carried out after first suitably protecting any potentially interfering reactive functional groups, as illustrated above or in the examples herein.

Advantageously, those starting materials should be used in said reactions, that lead to the formation of those compounds indicated above as being preferred.

Finally, the compounds of the invention are either obtained in the free form, or as a salt thereof. Any resulting base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention additionally relates to the use in mammals of the compounds of formula I and their pharmaceutically acceptable, non-toxic acid addition salts, or pharmaceutical compositions thereof, as medicaments, especially as psychotropic agents for the treatment of or management of central nervous system disorders responsive to benzodiazepine receptor stimulation, for example anxiety, and as anticonvulsant agents for the treatment of convulsive conditions (epilepsy).

The present invention also relates to the use of the compounds of the invention for the preparation of pharmaceutical compositions, especially anxiolytic and anticonvulsant pharmaceutical compositions.

The pharmaceutical compositions according to the invention are those suitable for enteral, such as oral or rectal, transdermal and parenteral administration to mammals, including man, comprising an effective amount of a pharmacologically active compound of formula I or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid or its magnesium or calcium salts, and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other thereapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of formula I with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

More specifically, the invention also relates advantageously to the method of treatment of disorders in mammals responsive to benzodiazepine receptor stimulation using an effective amount of a compound of the invention (or formula I or a pharmaceutically acceptable salt thereof), preferably in the form of above-cited pharmaceutical compositions. The dosage of active compound administered is dependent on the species of warm-blooded animal (mammal), the body weight, age and individual condition, and on the form of administration.

A unit dosage for a mammal of about 50 to 70 kg may contain between about 1 and 50 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, e.g. microanalysis and spectroscopic characteristics (e.g. IR, NMR).

EXAMPLE 1

3-(2-Pyridinyl)-9H-pyrrolo[2,1-c]-1,2,4-triazolo[4,3-a][1,4]benzodiazepine Hydrochloride Under an atmosphere of nitrogen, a slurry of 575 g of 11-chloro-5H-pyrrolo[2,1-c][1,4]benzodiazepine in 7.2 L of anhydrous ethanol is stirred while 364 g of pyridine-2-carboxylic acid hydrazide is added over a period of five minutes. The mixture is heated slowly to 65°. An exothermic reaction occurs and there is vigorous refluxing. When the refluxing subsides to a normal rate heating is continued and the mixture is stirred and refluxed for 21–22 hours. The product precipitates from the hot solution during the reflux period. The crystals are filtered off and washed on the filter with anhydrous ethanol. The product is air-dried overnight, then dried at high vacuum without heat for 2 days to yield 3-(2-pyridinyl)-9H-pyrrolo[2,1-c]-1,2,4-triazolo[4,3-a][1,4benzodiazepine hydrochloride, m.p. 265°–268° (d).

The starting materials are prepared as follows:

A solution of 2469 g of trichloroacetyl chloride in 2.7 L of anhydrous ether, in an atomsphere of nitrogen, is cooled in a water bath while a solution of 875 g of pyrrole is added over a period of 5¼ hours. The reaction mixture is stirred for one hour, then a solution of 1184 g of potassium carbonate in 3.3 L of water is added over a period of 1 hour at such a rate that the refluxing and foaming is kept at a minimum. After stirring another 2 hours, the reaction mixture is allowed to stand at room temperature overnight and then filtered through filter-cel. The ether layer is separated and the aqueous layer is extracted with 200 mL of ether.

The combined ether layers are stirred with 500 g of anhydrous magnesium sulfate and 19 g of charcoal, then filtered. The filtrate is concentrated to dryness in vacuo to yield 2-(trichloroacetyl)-pyrrole, m.p. 74°–75°.

A solution of sodium methoxide, prepared by dissolving sodium (34.0 g) in 4.0 L of methanol, is added to a solution of 2480 g of 2-(trichloroacetyl)-pyrrole in 6.0 L of methanol over a period of 1.5 hours under an atmosphere of nitrogen. There is an exotherm to 35° during the addition. Stirring is continued at room temperature for 2.5 hours, then the solution is concentrated to dryness in vacuo. The residue is dissolved in 9.0 L of ether and the solution is washed with 2×700 mL of water, dried over anhydrous magnesium sulfate (250 g), and stirred for 1 hour with charcoal (20 g). The mixture is filtered and the filtrate is concentrated to dryness to vacuo to give methyl pyrrole-2-carboxylate, m.p. 73°–74′.

Under an atmosphere of nitrogen, a solution of 700 g of methyl pyrrole-2-carboxylate in 3.5 L of dimethylformamide is added to a solution of 623 g of potassium t-butoxide in 3.5 L of dimethylformamide over a period of 10 minutes without any cooling. The reaction temperature rises to 35° during the addition.

After stirring at room temperature for one hour the mixture is cooled in a cold-water bath to 25°. Keeping the reaction temperature at about 25°, a solution of 976 g of 2-nitrobenzyl chloride in 3.5 L of dimethylformamide is added over a period of 40 minutes. The mixture is stirred at room temperature for 2 hours, then cooled to 9° and diluted with 14 L of cold water. After stirring for 2 hours, the mixture is allowed to stand at room temperature overnight. The crystals are filtered off and washed with 1 L of water. Air-drying for 48 hours gives methyl 1-(2-nitrobenzyl)-pyrrole-2-carboxylate, m.p. 105°–107°.

A mixture of 1117 g methyl 1-(2-nitrobenzyl)-pyrrole-2-carboxylate in 1117 mL of tetrahydrofuran, 458 g of potassium carbonate in 840 mL of water and 19 g of 5% palladium on carbon is stirred and heated to a temperature of 60°. The heat is removed and a solution of 1876 g of sodium hypophosphite hydrate in 3725 mL of water is added slowly over a period of one hour. The refluxing is controlled by the rate of the addition. When the addition is complete the mixture is refluxed, with stirring, for 2 hours. After stirring at room temperature for 5 hours, the reaction mixture is allowed to stand overnight. Methylene chloride (4 L) is added, the mixture is stirred for 3 hours and then filtered through filter-cel. The methylene chloride layer is separated and dried over magnesium sulfate. The magnesium sulfate is filtered off and the filtrate is concentrated to dryness to give a residue which is dried at 40°–50° and high vacuum to yield methyl 1-(2-aminobenzyl)-pyrrole-2-carboxylate, m.p. 95°–97°.

Under nitrogen, 322 g of methyl 1-(2-aminobenzyl)-pyrrole-2-carboxylate is stirred in 2 L of toluene while 157 g of potassium tert-butoxide is added all at once. The mixture is stirred under reflux for 3 hours, then stirred at room temperature overnight, chilled to 10° in an ice bath, and 750 mL of water is added. The solid is filtered off, washed with toluene and air-dried to yield 10,11-dihydro-5-H-pyrrolo([2,1-c][1,4]benzodiazepine-11-one, m.p. 214°–215°.

A slurry of 881 g of 10,11-dihydro-5-H-pyrrolo-[2,1-c][1,4]benzodiazepin-11-one is stirred in 12 L of methylene chloride, and 819 g of 99% phosphorus oxychloride is added all at once. The mixture is stirred and refluxed for 19 hours. The reaction mixture is cooled to room temperature. A mixture of 5 L of crushed ice, 7.5 L of cold water and 1.81 kg of 28% ammonium hydroxide solution is stirred and 1.25 L portions of the reaction mixture are added over a period of 15 minutes. The reaction temperature is kept below 25° during the addition. After stirring for 15 minutes, the layers are separated, the methylene chloride layer is washed by stirring with 1 L of cold water then dried by stirring with magnesium sulfate for 1 hour. Charcoal (90 g) is added and the mixture is filtered through filter-cel. The methylene chloride solution is concentrated to dryness in vacuo to give 11-chloro-5H-pyrrolo[2,1-c][1,4]benzodiazepine, m.p. 102°-104°.

Pyridine-2-carboxylic acid hydrazide is prepared as follows: 230 g (228 mL) of anhydrous hydrazine is added, over a period of 10–15 minutes, to a stirred solution of 977.4 g of ethyl pyridine-2-carboxylate ((ethyl picolinate) in 1750 mL of anhydrous ethanol. The reaction is exothermic. The solution is stirred and refluxed for 5 hours, then stirred at room temperature overnight. The crystalline product is filtered off, washed first with anhydrous alcohol and then with anhydrous ether, and air-dried to yield pyridine-2-carboxylic acid hydrazide, m.p. 95°-100°.

EXAMPLE 2

3-(2-Pyridinyl)-9H-pyrrolo[2,1-c]-1,2,4-triazolo[4,3-a][1,4]benzodiazepine (a) Into a suitable reactor are charged N,N-dimethylformamide (159 kg) and 2-pyridinecarboxylic acid hydrazide (25.2 kg) and the mixture is stirred 10–15 minuted at 20°-25° to give a solution. In a separate suitable reactor are charged N,N-dimethylformamide (97 kg) and 11-chloro-5H-pyrrolo-[2,1-c][1,4]benzodiazepine (34.4 kg). The mixture is stirred for 15–30 minutes at 20°-25° to give a solution. This solution is added over 2–3 hours to the preheated solution of 2-pyridinecarboxylic acid hydrazide in N,N-dimethylformamide at 48° to 52°. Once the addition is complete the reaction mixture is further stirred for 2–3 hours at 48° to 52°. The reaction mixture is then heated for 12–15 hours at 72°-75°. The mixture is then cooled to 15°-20° with stirring. The solid is filtered off and washed with N,N-dimethylformamide (28 L). The solid is then stirred in a 1:1 mixture of water and ethanol (140 L) for 30–60 minutes at 20°-25°. The pH is adjusted to about 7 using concentrated ammonium hydroxide solution. The reaction mixture is stirred for 30–60 minutes at 20°-25°. The solid is filtered off, washed with a mixture of ethanol and water (1:1, 50 L) and vacuum dried (60°-70°) to give the title compound as the free base, m.p. 255°-257°.

(b) The dihydrochloride salt has m.p. 245°-248°; the sulfate salt has m.p. 205°-207°.

EXAMPLE 3

6-Chloro-3-(2-pyridinyl)-9H-pyrrolo[2,1-c]-1,2,4-triazolo[4,3-a][1,4]benzodiazepine Hydrochloride A mixture of 1.26 g of 8,11-dichloro-5H-pyrrolo[2,1-c][1,4]benzodiazpine, 900 mg of pyridine-2-carboxylic acid hydrazide in 50 mL anhydrous ethanol is heated at reflux temperature for approximately 18 hours. The solvent is removed by evaporation under reduced pressure and the residue triturated with 50 mL of a 1:1 mixture of diethyl ether and isopropanol. After decanting the supernatant solvent, the residue is made basic with 10% sodium hydroxide solution and extracted (2×200 mL) with methylene chloride. The combined methylene chloride extracts are dried over anhydrous magnesium sulfate, filtered and the solvent removed by evaporation under reduced pressure. The solid residue is dissolved in 30 mL of a 4N ethanolic solution of hydrogen chloride. The resulting 6-chloro-3-(2-pyridinyl)-9H-pyrrolo[2,1-c]-1,2,4-triazolo[4,3-a][1,4]-benzodiazepine hydrochloride is collected by filtration, m.p. >260°.

The starting material is prepared as follows:

To a stirred solution of 10 g of 4-chloro-2-nitrobenzyl alcohol in 200 mL of ether is added dropwise a solution of 17.7 g phosphorus tribromide in 100 mL of ether. The temperature of the reaction mixture is maintained at 15° or lower by means of cooling with an ice-water bath. On completion of the addition the reaction mixture is allowed to stir for an additional 1 hour at 15° and then at room temperature overnight. The reaction mixture is neutralized with 100 mL of 3N sodium hydroxide, and the layers are separated. The ethereal extracts are washed with 2×250 mL of brine, dried over anydrous sodium sulfate; the solvent is evaporated to dryness under reduced pressure to yield 4-chloro-2-nitrobenzyl bromide melting at 50°.

To a solution of 493 mg of potassium tert-butoxide in 5 mL of dimethylformamide (anhydrous) is added dropwise a solution of 556 mg of ethyl pyrrole-2-carboxylate (prepared as described in Organic Synthesis, Vol. 51, p. 100) in 5 mL of anhydrous dimethylformamide. On completion of the addition the mixture is allowed to stir at room temperature for 1 hour. To this mixture is added a solution of 1 g of 4-chloro-2-nitrobenzyl bromide in 5 mL of dimethylformamide. The reaction mixture is then heated to 75° and maintained at this temperature for 18 hours, then allowed to cool to room temperature. The reaction mixture is poured into 20 mL of ice-water and extracted with 2×30 mL of ether. The combined ethereal extracts are washed with 2×30 mL of water followed by 30 mL of saturated sodium bicarbonate solution. The ethereal extracts are dried over anhydrous sodium sulfate and the solvent evaporated under reduced pressure to yield ethyl 1-(4-chloro-2-nitrobenzyl)-pyrrole-2-carboxylate melting at 104°-106°.

To a solution of 18.0 g thereof in 200 mL ethyl acetate is added 1.8 g of platinum oxide as catalyst and the mixture is subjected to hydrogenation in a Parr apparatus at 3 atmospheres pressure until the required amount of hydrogen is absorbed. The catalyst is removed by filtration and the solvent removed by evaporation under reduced pressure to yield ethyl 1-(4-chloro-2-aminobenzyl)-pyrrole-2-carboxylate melting at 104°-107°.

To a solution of 11.2 g thereof in 200 mL of xylene is added 48 g of sodium methoxide and the reaction mixture is heated at reflux temperature for 4 hours. The reaction is then allowed to cool to room temperature and the solvent is removed by evaporation under reduced pressure. To the residue is added 100 mL of ice-water and the product is collected to yield 8-chloro-10,11-dihydro-5-H-pyrrolo -[2,1-c][1,4]benzodiazepin-11-one melting at 225°-299°.

To a suspension of 900 mg thereof in 50 mL toluene is added 804 mg of phosphorus pentachloride. The mixture is heated to reflux and maintained at this temperature for 2 hours. The reaction mixture is allowed to cool to room temperature, filtered, and poured into 100 mL of saturated sodium carbonate solution. The toluene extract is dried over anhydrous sodium sulfate and evaporated to dryness. The residue is digested with 200 mL of ether and the solution filtered. The filtrate is decolorized with charcoal and evaporated to dryness to yield 8,11-dichloro-5H-pyrrolo[2,1-c][1,4]benzodiazepine melting at 129°-135°.

EXAMPLE 4

6-Trifluoromethyl-3-(2-pyridinyl)-9H-pyrrolo[2,1-c]-1,2,4-triazolo[4,3-a][1,4]benzodiazepine Hydrochloride A mixture of 1.43 g of 11-chloro-8-trifluoromethyl-5H-pyrrolo[2,1-c][1,4]benzodiazepine, 822 mg of pyridine-2-carboxylic acid hydrazide in 20 mL anhydrous ethanol is heated at reflux temperature for approximately 18 hours. The solvent is removed and the residue is triturated with 50 mL of a 1:1 mixture of diethyl ether and isopropanol. After decanting the supernatant liquid, 10% aqueous sodium hydroxide solution is added to the residue and the product is extracted with 2×150 mL of methylene chloride. The combined methylene chloride extracts are washed with 2×150 L of water, are dried over anydrous magnesium sulfate, and evaporated under reduced pressure. The residue is dissolved in 30 mL of 4N ethanolic solution of hydrogen chloride, and 6-trifluoromethyl-3-(2-pyridinyl)-9H-pyrrolo[2,1-c]-1,2,4-triazolo[4,3-a][1,4]benzodiazepine hydrochloride, m.p.>250°, crystallizes out.

The starting material is prepared in an analogous manner to that described in the previous examples starting with 4-trifluoromethyl-2-nitrobenzyl bromide.

EXAMPLE 5

6-Chloro-12-methyl-3-(2-pyridinyl)-9H-pyrrolo[2,1-c]-1,2,4-triazolo[4,3-a][1,4]benzodiazepine Hydrochloride A mixture of 740 mg of 8,11-dichloro-2-methyl-5H-pyrrolo[2,1-c][1,4]benzodiazepine, 382 mg of pyridine-2-carboxylic acid hydrazide in 20 mL anhydrous ethanol is heated at reflux temperature for 24 hours. The reaction mixture is then cooled to 0° (ice-bath) and diluted with 50 mL of diethyl ether. 6-Chloro-12-methyl-3-(2-pyridinyl)-9-H-pyrrolo[2,1-c]-1,2,4-triazolo[4,3-a][1,4]-benzodiazepine hydrochloride which crystallizes out is collected, m.p.>250°.

The starting material is prepared as follows:

To a stirred solution of 2.33 g of 8-chloro-10,11-dihydro-5H-pyrrolo[2,1-c][1,4]benzodiazepin-11-one in 50 mL of methylene chloride is added 5.33 g of aluminum trichloride in small aliquots over a 30 minute period. During this time the temperature of the reaction is maintained below 30°. To this reaction mixture 4 mL of methyl iodide is added, and the reaction is allowed to stir for 48 hours at room temperature. The reaction mixture is diluted with 24 mL of methanol and then poured into 150 mL of dilute hydrochloric acid. The methylene chloride layer is separated and washed with 200 mL of brine and saturated aqueous sodium bicarbonate. The methylene chloride extract is dried over anhydrous magnesium sulfate and evaporated to dryness to yield 8-chloro-2-methyl-10,11-dihydro-5-H-pyrrolo-[2,1-c][1,4]benzodiazepine-11-one, which was used without further purification.

To a suspension of 1.1 g of 8-chloro-2-methyl-10,11-dihydro-5H-pyrrolo[2,1-c][1,4]benzodiazepine-11-one in 20 mL of chlorobenzene is added 680 mg of phosphorous oxychloride. The mixture is heated at 100°-110° for 1 hour, then allowed to cool to room temperature. Methylene chloride (150 mL) is added to the stirred reaction mixture which is then poured into a mixture of ice and aqueous sodium carbonate. After being shaken vigorously, the methylene chloride layer is separated, the aqueous layer is further extracted with 200 ml of diethyl ether; the combined extracts are dried (anhydrous magnesium sulfate), decolorized with charcoal, and evaporated to dryness to yield 8,11-dichloro-2-methyl-5H-pyrrolo[2,1-c][1,4]benzodiazepine as a viscous oil which is used in the next step without further purification.

EXAMPLE 6

11-Chloro-3-(2-pyridinyl)-9H-pyrrolo[2,1-c]-1,2,4-triazolo[4,3-a][1,4]benzodiazepine Hydrochloride A mixture of 1.27 g of 3,11-dichloro-5-pyrrolo-]2,1-c]-[1,4]benzodiazepine and 700 mg of pyridine-2-carboxylic acid hydrazide in 50 mL of anhydrous ethanol is heated at reflux temperature for 24 hours. The reaction is then cooled to 0° (ice-bath) and diluted with 50 mL of ethyl ether. The product, 11-chloro-3-(2-pyridinyl)-9H-pyrrolo[2,1-c]1,2,4-triazolo[4,3-a][1,4]benzodiazepine hydrochloride which crystallizes out, is collected by filtration, m.p. 230°-239°.

The starting material is prepared as follows:

To a solution of 2.5 g of methyl 1-(2-nitrobenzyl)pyrrole-2-carboxylate in 50 mL of dry tetrahydrofuran is added 1.54 g of N-chlorosuccinimide. The reaction is allowed to stir at room temperature for 48 hours. To the reaction mixture is added sodium sulfite, the reaction is stirred for an additional 1 hour, filtered and evaporated to dryness. The residue is extracted into 200 mL of ether, the extract is dried over anhydrous magnesium sulfate and evaporated to dryness to yield methyl 1-(2-nitrobenzyl)-5-chloropyrrole-2-carboxylate which is used in the next step without further purification.

To a stirred solution of 2.68 g of methyl 1-(2-nitrobenzyl)-5-chloropyrrole-2-carboxylate in 30 mL of anhydrous tetrahydrofuran is added 35 mL of titanium trichloride in a dropwise manner over a 15 minute period. The reaction is allowed to stir at room temperature for 18 hours and then is diluted with 150 mL of a 1:1 mixture of diethyl ether and water. The organic phase is separated, washed with brine and saturated sodium bicarbonate, dried over anhydrous sodium sulfate, and evaporated to dryness to yield methyl 1-(2-aminobenzyl)-5-chloropyrrole-2-carboxylate which is used in the next step without further purification.

To a stirred solution of 2.3 g of methyl 1-(2-aminobenzyl)-5-chloropyrrole-2-carboxylate in 30 mL of methylene chloride is added 12.4 mL of trimethylaluminum dropwise over a period of 15 minutes. On completion of the addition the reaction mixture is allowed to stir overnight at room temperature. The reaction is then cooled to 0° (ice-bath) and 20 mL of water is added in a dropwise manner. The methylene chloride is removed by evaporation under reduced pressure, 20 mL of 6N HCl is added to the residue and the mixture is stirred for an additional 1 hour. The precipitated product, 3-chloro-10,11-dihydro-5H-pyrrolo[2,1-c][1,4]benzodiazepin-11-one is used in the next step without further purification.

The conversion to 3,11-dichloro-5-H-pyrrolo[2,1-c]-[1,4]benzodiazepine is carried out in an analogous manner to that described herein for the preparation of e.g. 11-chloro-5-H-pyrrolo[1,2-c][1,4]benzodiazepine.

EXAMPLE 7

Compounds of formula II which are prepared according to methods analogous to those described in the previous examples using the appropriate starting materials, e.g. of formula IIIa wherein X'=chloro and the corresponding optionally substituted pyridine-2-, 3- or 4-carboxylic acid hydrazides;

(a) 6-chloro-3-(3-pyridinyl)-9H-pyrrolo[2,1-c]-1,2,4-triazolo[4,3-a][1,4]benzodiazepine dihydrochloride, m.p.>250°;

(b) 6-chloro-3-(4-pyridinyl)-9H-pyrrolo[2,1-c]-1,2,4-triazolo[4,3-a][1,4]benzodiazepine, m.p.>250°;

(c) 6-chloro-3-[2-(4-butylpyridinyl)]-9H-pyrrolo-[2,1-c]-1,2,4-triazolo[4,3-a][1,4]benzodiazepine hydrochloride, m.p. 205°-210°;

(d) 6-trifloromethyl-3-(4-pyridinyl)-9H-pyrrolo-[2,1-c]-1,2,4-triazolo[4,3-a][1,4]benzodiazepine hydrochloride, m.p.>250°;

(e) 6-trifluoromethyl-3-(3-pyridinyl)-9H-pyrrolo-[2,1-c]-1,2,4-triazolo[4,3-a][1,4]benzodiazepine hydrochloride, m.p.>250°;

(f) 6,7-dimethoxy-3-(2-pyridinyl)-9H-pyrrolo[2,1-c]-1,2,4-triazolo[4,3-a][1,4]benzodiazepine hydrochloride, m.p. 233°-234°;

(g) 6,12-dichloro-3-(2-pyridinyl)-9H-pyrrolo[2,1-c]-1,2,4-triazolo[4,3-a][1,4]benzodiazepine, m.p.>250°.

The 2,8-dichloro-10,11-dihydro-5H-pyrrolo[2,1-c]-[1,4]benzodiazepin-11-one intermediate for compound 7 g) is prepared as follows:

To a solution of 2.33 g of 8-chloro-10,11-dihydro-5H-pyrrolo[2,1-c][1,4]benzodiazepin-11-one in 50 mL of methylene chloride is added 5.33 g of aluminum trichloride. The reaction is stirred for 1 hour at room temperature and 0.77 mL (1.2 g) of methanesulfonyl chgloride is added. Stirring is then continued at room temperature overnight. The reaction mixture is basified with 10% ammonium hydroxide and the resulting solid collected by filtration. The solid is dissolved in methylene chloride, the solution is washed with water, dried over magnesium sulfate and evaporated to dryness to yield 2,8-dichloro-10,11-dihydro-5H-pyrrolo[2,1-c][1,4]-benzodiazepin-11-one, which is used without further purification.

EXAMPLE 8

Compounds of formula I which are prepared according to methods analogous to those described in the previous examples using appropriate starting materials, e.g. of formula IIIa wherein X'=chloro and the unsubstituted or the corresponding substituted benzoic acid hydrazides:

(a) 6-trifluoromethyl-3-phenyl-9H-pyrrolo[2,1-c]-1,2,4-triazolo[4,3-a][1,4]benzodiazepine hydrochloride, m.p.>250°;

(b) 3-(2-fluorophenyl)-9H-pyrrolo[2,1-c]-1,2,4-triazolo[4,3-][1,4]benzodiazepine hydrochloride, m.p. 225°-230°;

(c) 3-(3-trifluoromethylphenyl)-9H-pyrrolo[2,1-c]-1,2,4-triazolo[4,3-a][1,4]benzodiazepine hydrochloride, m.p. 221°-225°;

(d) 3-phenyl-9H-pyrrolo[2,1-c]-1,2,4-triazolo[4,3-a][1,4]benzodiazepine hydrochloride, m.p. >250°;

(e) 3-(2-chlorophenyl)-9H-pyrrolo[2,1-c]-1,2,4-triazolo[4,3-a][1,4]benzodizepine hydrochloride, m.p. >250°.

(f) 6-chloro-3-phenyl-9H-pyrrolo[2,1-c]-1,2,4-triazolo[4,3-a][1,4]benzodiazepine hydrochloride, m.p. >250°;

(g) 6-chloro-3-(3-chlorophenyl)-9H-pyrrolo[2,1-c]-1,2,4-triazolo[4,3-a][1,4]benzodiazepine hydrochloride, m.p. >250°;

(h) 6-trifluoromethyl-3-(3-trifluoromethylphenyl)-9H-pyrrolo[2,1-c]-1,2,4-triazolo[4,3-a][1,4]benzodiazepine hydrochloride, m.p. >250°;

(i) 6-trifluoromethyl-3-(2-chlorophenyl)-9H-pyrrolo[2,1-c]-1,2,4-triazolo[4,3-a][1,4]benzodiazephine hydrochloride, m.p. >250°;

(j) 6-chloro-3-(2-fluorophenyl)-9H-pyrrolo[2,1-c]-1,2,4-triazolo[4,3-a][1,4]benzodiazepine hydrochloride, m.p. 236°-237°;

(k) 6-chloro-3-(2-chlorophenyl)-9H-pyrrolo[2,1-c]-1,2,4-triazolo[4,3-a][1,4]benzodiazepine hydrochloride, m.p. 254°-255°;

(l) 6-chloro-3-(3-trifluoromethylphenyl)-9H-pyrrolo[2,1-c]-1,2,4-triazolo[4,3-a][1,4]benzodiazepine hydrochloride, m.p. >250°;

(m) 6-chloro-3-(3-chlorophenyl)-9H-pyrrolo[2,1-c]-1,2,4-triazolo[4,3-a][1,4]benzodiazepine hydrochloride, m.p. 22 250°;

(n) 6,7-dimethoxy-3-(2-fluorophenyl)-9H-pyrrolo[2,1-c]-1,2,4-triazolo[4,3-a][1,4]benzodiazepine hydrochloride, m.p. 227°-229°.

EXAMPLE 9

Compounds of formula I which are prepared according to methods analogous to those described in the previous examples using appropriate starting materials, e.g. of formula IIIa wherein X'=chloro and the unsubstituted or correspondingly substituted 2,-, 3-, or 4-quinolinecarboxylic acid hydrazides.

(a) 6-trifluoromethyl-3-(2-quinolinyl)-9H-pyrrolo[2,1-c]-1,2,4-triazolo[4,3-a][1,4]benzodiazepine hydrochloride, m.p. >250°;

(b) 6-chloro-3-(2-quinolinyl)-9H-pyrrolo[2,1-c]-1,2,4-triazolo[4,3-a][1,4]benzodiazepine hydrochloride, m.p. 239°-240°;

(c) 3-(4-hydroxy-3-quinolinyl)-9H-pyrrolo[2,1-c]-1,2,4-triazolo[4,3-a][1,4]benzodiazepine hydrochloride, m.p. >250°;

(d) 3-(4-hydroxy-6-fluoro-3-quinolinyl)-9H-pyrrolo[2,1-c]-1,2,4-triazolo[4,3-a][1,4]benzodiazepine hydrochloride, m.p. >250°;

(e) 3-(4-quinolinyl)-9H-pyrrolo[2,1-c]-1,2,4-triazolo[4,3-a][1,4]benzodiazepine.

EXAMPLE 10

Compounds of formula I which are prepared according to methods analogous to those described in the previous examples using appropriate starting materials, e.g. of formula IIIa wherein X'=chloro and the unsubstituted or correspondingly substituted 2- or 3-pyrrolecarboxylic acid hydrazides:

(a) 6-trifluoromethyl-3-(2-pyrrolyl)-9H-pyrrolo[2,1-c]-1,2,4-triazolo[4,3-a][1,4]benzodiazepine hydrochloride, m.p. >250°;

(b) 3-(2-pyrrolyl)-9H-pyrrolo[2,1-c]-1,2,4-triazolo[4,3-a][1,4]benzodiazepine hydrochloride, m.p. 250°-253°;

(c) 6-chloro-3-(2-pyrrolyl)-9H-pyrrolo[2,1-c]-1,2,4-triazolo[4,3-a][1,4]benzodiazepine hydrochloride, m.p. >250°;

(d) 6-chloro-3-[2-(1-methylpyrrolyl)]-9H-pyrrolo[2,1-c]-1,2,4-triazolo[4,3-a][1,4]benzodiazepine hydrochloride, m.p. 250°;
(e) 3-(3-pyrrolyl)-9H-pyrrolo[2,1-c]-1,2,4-triazolo[4,3-a][1,4]benzodiazepine.

EXAMPLE 11

Compounds of formula I which are prepared according to methods analogous to those described in the previous examples using appropriate starting materials, e.g. of formula IIIa wherein X'=chloro and the 2- or 3-thiophenecarboxylic acid hydrazides:
(a) 6-chloro-3-(2-thienyl)-9H-pyrrolo[2,1-c]-1,2,4-triazolo[4,3-a][1,4]benzodiazepine hydrochoride, m.p. >250°;
(b) 3-(3-thienyl)-9H-pyrrolo[2,1-c]-1,2,4triazolo[4,3-a][1,4]benzodiazepine.

EXAMPLE 12

Compounds of formula I which are prepared according to methods analogous to those described in the previous examples using the appropriate starting materials, e.g. of formula IIIa wherein X'=chloro and the 2- or 3-furancarboxylic acid hydrazides:
(a) 6-chloro-3-(3-furanyl)-9H-pyrrolo[2,1-c]-1,2,4-triazolo[4,3-a][1,4]benzodiazepine;
(b) 3-(2-furanyl)-9H-pyrrolo[2,1-c]-1,2,4-triazolo[4,3-a][1,4]benzodiazepine.

EXAMPLE 13

Compounds of formula I which are prepared according to methods analogous to those described in the previous examples using the appropriate starting materials, e.g. of formula IIIa e.g. wherein X'=chloro and the isoquinoline-3-carboxylic acid hydrazides:
(a) 3-(3-isoquinolyl)-9H-pyrrolo[2,1-c]1,2,4-triazolo-[4,3-a][1,4]benzodiazepine;
(b) 6-chloro-3-(3-isoquinolyl)-9H-pyrrolo[2,1-c]-1,2,4-triazolo-[4,3-a][1,4]benzodiazepine.

EXAMPLE 14

Compounds of formula I which are prepared according to methods analogous to those described in the previous examples using the appropriate starting materials, e.g. of formula IIIa wherein X'=chloro and the pyrazine-2-carboxylic acid hydrazides:
(a) 3-(2-pyrazinyl)-9H-pyrrolo[2,1-c]-1,2,4-triazolo[4,3-a][1,4]benzodiazepine;
(b) 6-chloro- 3-(2-pyrazinyl)-9H-pyrrolo[2,1-c]-1,2,4-triazolo[4,3-a][1,4]benzodiazepine.

EXAMPLE 15

To a suspension of 3 g of 3-(2-pyridinyl)-9H-pyrrolo[2,1-c]-1,2,4-triazolo[4,3-a][1,4]benzodiazepine in 50 mL of tetrahydrofuran is added 1.8 g of N-bromosuccinimide. The reaction mixture is allowed to stir at room temperature for 3 hours during which time a heavy white precipitate forms. A solution of aqueous sodium bisulfite is added to the reaction mixture and, after stirring for an additional 1 hour, the solid is collected and washed with 100 ml of water. The filtrate is evaporated to dryness under reduced pressure to yield a white solid. The combined solids are dissolved in 150 mL of methylene chloride, the solution is drived over anhydrous magnesium sulfate, filtered, and the solvent is evaporated under reduced pressure to yield 11-bromo-3-(2-pyridinyl)-9H-pyrrolo[2,1-c]-1,2,4-triazolo[4,3-a][1,4]benzodiazepine, m.p. 228°-229° (d). Product is recrystallized from a mixture of methylene chloride and diethyl ether.

EXAMPLE 16

A mixture of 1.3 g of 11-bromo-3-(2-pyridinyl)-9H-pyrrolo[2,1-c]-1,2,4-triazolo[4,3-a][1,4]benzodiazepine in 50 mL of methanol and 400 mg of 10% palladium on charcoal is hydrogenated at 3 atmospheres pressure for 7 hours at room temperature.

On completion of the hydrogenation, the catalyst is removed by filtration and the solvent evaporated under reduced pressure. Residue is triturated in water, the resulting solid is collected, washed with 10% ammonium hydroxide and water, and dissolved in methylene chloride. The methylene chloride solution is dried over magnesium sulfate and evaporated to dryness. The residue is crystallized by trituration with ethyl ether/methylene chloride to give 3-(2-pyridinyl)-9H-pyrrolo[2,1-c]-1,2,4-triazolo[4,3-a][1,4]benzodiazepine.

EXAMPLE 17

Preparation of 1,000 capsules each containing 10 mg of the active ingredient:
Formula:

| | |
|---|---|
| 3-(2-Pyridinyl)-9H—pyrrolo[2,1-c]-1,2,4-triazolo[4,3-a][1,4]benzodiazepine | 10.0 g |
| Lactose | 210.0 g |
| Modified starch | 77.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously capsules are prepared, containing about 1-50 mg of the other compounds disclosed and illustrated herein.

EXAMPLE 18

Preparation of 10,000 tablets each containing 5 mg of the active ingredient:
Formula:

| | |
|---|---|
| 6-Chloro-3-(2-pyridinyl)-9H—pyrrolo[2,1-c]-1,2,4-triazolo[4,3-a][1,4]benzodiazepine | 50.00 g |
| Lactose | 1,535.00 g |
| Corn starch | 125.00 g |
| Polyethylene glycol 6,000 | 150.00 g |
| Talcum powder | 50.00 g |
| Magnesium stearate | 40.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen and compressed into tablets, using concave punches uppers bisected.

Analogously tablets are prepared, containing about 1–50 mg of one of the other compounds illustrated by the previous examples.

What is claimed is:

1. A compound of the formula

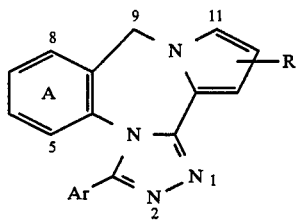

wherein ring A is unsubstituted or substituted by one or two identical or different substituents selected from lower alkyl, halogen, trifluoromethyl, lower alkoxy, hydroxy and acyloxy; or ring A is substituted on adjacent carbon atoms by lower alkylenedioxy; R represents hydrogen, halogen or lower alkyl; Ar represents (a) phenyl or phenyl substituted by one or two identical or different substituents selected from lower alkyl, halogen, trifluoromethyl, lower alkoxy, hydroxy and acyloxy; or phenyl sustituted on adjacent carbon atoms by lower alkylenedioxy;

(b) naphthyl or naphthyl substituted by one or two identical or different substituents selected from lower alkyl, halogen, lower alkoxy, hydroxy and acyloxy;

(c) pyridinyl or pyridinyl substituted on carbon by one or two substituents selected from lower alkyl, lower alkoxy and halogen;

(d) pyrrolyl or pyrrolyl substituted on carbon by one or two substituents selected from lower alkyl, lower alkoxy and halogen; or said radical substituted on nitrogen by lower alkyl;

(e) quinolinyl of isoquinolinyl or each said radical substituted on carbon by one or two substituents selected from lower alkyl, lower alkoxy, halogen and hydroxy;

(f) imidazolyl or imidazolyl substituted on carbon by one substituent selected from lower alkyl and halogen; or said radical substituted on one nitrogen by lower alkyl;

(g) thienyl or thienyl substituted on carbon by one or two substituents selected from lower alkyl, lower alkoxy or halogen;

(h) furanyl or furanyl substituted on carbon by one or two lower alkyl groups;

(l) pyrimidinyl or pyrimidinyl substituted on carbon by one or two substituents selected from lower alkyl, lower alkoxy and halogen;

(j) pyrazinyl or pyrazinyl substituted on carbon by one or two lower alkyl groups;

(k) thiazolyl or thiazolyl substituted on carbon by one substituent selected from lower alkyl and halogen; and (l) indolyl or indolyl substituted on carbon by one or two substituents selected from lower alkyl, lower alkoxy and halogen; or said radical substituted on nitrogen by lower alkyl;

wherein the point of attachment of any of the said heteroaryl radicals is on a ring carbon; and wherein the point of attachment for pyrrolyl, indolyl or imidazolyl radicals unsubstituted on nitrogen may also be on ring nitrogen; and wherein within the above definitions acyloxy is in the form of a pharmaceutically acceptable ester; or a pharmaceutically acceptable salt thereof.

2. A compound of the formula

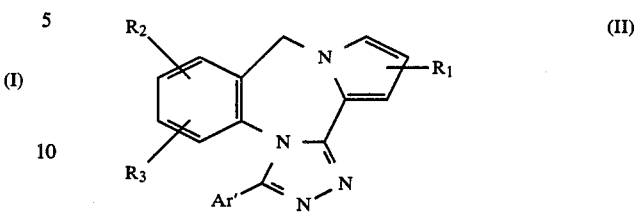

wherein Ar' represents 2-, 3- or 4-pyridinyl or 2-, 3- or 4-pyridinyl monosubstituted on carbon by lower alkyl, lower alkoxy or halogen; $R_1$ represents hydrogen, lower alkyl or halogen; $R_2$ and $R_3$ independently represent hydrogen, lower alkyl, halogen, trifluoromethyl, lower alkoxy, hydroxy, or acyloxy in form of a pharmaceutically acceptable ester; or $R_2$ and $R_3$ together on adjacent carbon atoms represent lower alkylenedioxy; or a pharmaceutically acceptable salt thereof.

3. A compound according to claim 2 wherein Ar' represents 2-, 3- or 4- pyridinyl; or a pharmaceutically acceptable salt thereof.

4. A compound according to claim 2 wherein Ar' represents 2-pyridinyl or 2-pyridinyl monosubstituted on carbon by lower alkyl, lower alkoxy or halogen; or a pharmaceutically acceptable salt thereof.

5. A compound according to claim 2 wherein Ar' represents 2-pyridinyl; $R_1$ represents hydrogen, lower alkyl or halogen; $R_2$ represents hydrogen, lower alkoxy, lower alkyl, halogen or trifluoromethyl; $R_3$ represents hydrogen, halogen, lower alkyl or lower alkoxy; $R_2$ and $R_3$ together on adjacent carbon atoms represent methylenedioxy; or a pharmaceutically acceptable salt thereof.

6. A compound according to claim 2 wherein Ar' represents 2-pyridinyl; $R_1$ represents hydrogen; $R_2$ represents hydrogen, halogen or trifluoromethyl; $R_3$ represents hydrogen; or a pharmaceutically acceptable salt thereof.

7. A compound according to claim 1 of formula I wherein ring A is unsubstituted or mono- or disubstituted independently of each other by halogen, lower alkyl or lower alkoxy; or monosubstituted by trifluoromethyl; R represents hydrogen; Ar represents phenyl or phenyl monosubstituted by halogen, trifluoromethyl or lower alkyl; or Ar represents 2- or 3-thienyl; or a pharmaceutically acceptable salt thereof.

8. A compound according to claim 7 wherein Ar represents phenyl or phenyl monosubstituted by halogen, trifluoromethyl or lower alkyl; or a pharmaceutically acceptable salt thereof.

9. A compound according to claim 7 wherein Ar represents 2- or 3-thienyl; or a pharmaceutically acceptable salt thereof.

10. A compound according to claim 2 being 3-(2-pyridinyl)-9H-pyrrolo[2,1-c]-1,2,4-triazolo[4,3-a][1,4]benzodiazepine or a pharmaceutically acceptable salt thereof.

11. A compound according to claim 2 being 6-chloro-3-(2-pyridinyl)-9H-pyrrolo[2,1-c]-1,2,4-triazolo [4,3-a][1,4]benzodiazepine or a pharmaceutically acceptable salt thereof.

12. A compound according to claim 2 being 6-chloro-3-(4-pyridinyl)-9H-pyrrolo(2,1-c]-1,2,4triazolo[4,3-l][1,4]benzodiazepine or a pharmaceutically acceptable salt thereof.

13. A compound according to claim 2 being 6-trifluoromethyl-3-(3-pyridinyl-9H-pyrrolo[2,1-c]-1,2,4-triazolo[4,3-a][1,4]benzodiazepine or a pharmaceutically acceptable salt thereof.

14. A pharmaceutical composition suitable for administration to mammals for the treatment of nervous system conditions responsive to benzodiazepine receptor stimulation, comprising an effective amount of a compound of claim 1 in combination with one or more inert pharmaceutically acceptable carriers.

15. A method for the treatment of convulsive disorders or anxiety responsive to benzodiazepine receptor stimulation in mammals which comprises administering to a mammal in need thereof an effective amount of a compound of claim 1 or of a pharmaceutical composition comprising said compound.

16. A method according to claim 15 for the treatment of convulsive disorders.

17. A method according to claim 15 for the treatment of anxiety.

18. A method according to claim 17 wherein the compound is 3-(2-pyridinyl)-9H-pyrrolo[2,1-c]-1,2,4-triazolo[4,3-a][1,4]benzodiazepine or a pharmaceutically acceptable salt thereof.

* * * * *